United States Patent
Murphy et al.

(10) Patent No.: US 10,011,807 B2
(45) Date of Patent: Jul. 3, 2018

(54) FABRIC SOFTENER COMPOSITIONS

(71) Applicant: Stepan Company, Northfield, IL (US)

(72) Inventors: Dennis R. Murphy, Libertyville, IL (US); Leonard F. Zaporowski, Arlington Heights, IL (US); Christopher A. Gariepy, Northbrook, IL (US); Carmen Matache, Mount Prospect, IL (US); Diana J. Dardugno, Palatine, IL (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 15/173,188

(22) Filed: Jun. 3, 2016

(65) Prior Publication Data

US 2016/0281033 A1    Sep. 29, 2016

Related U.S. Application Data

(63) Continuation of application No. 14/853,500, filed on Sep. 14, 2015, now abandoned, which is a continuation of application No. PCT/US2013/065477, filed on Oct. 17, 2013.

(60) Provisional application No. 61/789,825, filed on Mar. 15, 2013.

(51) Int. Cl.
| | |
|---|---|
| *C11D 1/62* | (2006.01) |
| *C11D 3/00* | (2006.01) |
| *C11D 3/20* | (2006.01) |
| *C11D 3/30* | (2006.01) |
| *C07C 213/02* | (2006.01) |
| *C07C 213/06* | (2006.01) |
| *C11D 7/32* | (2006.01) |
| *C11D 11/00* | (2006.01) |

(52) U.S. Cl.
CPC .......... *C11D 3/0015* (2013.01); *C07C 213/02* (2013.01); *C07C 213/06* (2013.01); *C11D 1/62* (2013.01); *C11D 3/2079* (2013.01); *C11D 3/2093* (2013.01); *C11D 3/30* (2013.01); *C11D 7/3209* (2013.01); *C11D 11/0017* (2013.01)

(58) Field of Classification Search
CPC .......... C11D 3/0015; C11D 1/62; C11D 3/30; C07C 213/06
See application file for complete search history.

(56) References Cited

U.S. PATENT DOCUMENTS

| | | |
|---|---|---|
| 6,180,594 B1 | 1/2001 | Fender et al. |
| 6,410,503 B1 | 6/2002 | Masschelein |
| 6,875,735 B1 | 4/2005 | Frankenbach |
| 8,026,206 B2 | 9/2011 | Sajic et al. |
| 2006/0234891 A1 | 10/2006 | Noyes et al. |
| 2007/0054835 A1 | 3/2007 | Corona, III et al. |
| 2010/0197560 A1 | 8/2010 | Nepras et al. |
| 2013/0059767 A1 | 3/2013 | Subramanam et al. |
| 2015/0307812 A1 | 10/2015 | Schramm ,Jr. et al. |
| 2015/0315521 A1 | 11/2015 | Schramm, Jr. et al. |

FOREIGN PATENT DOCUMENTS

| | | | |
|---|---|---|---|
| JP | 2005-023123 A | * | 1/2005 |
| JP | 2005-023123 A | | 1/2005 |
| JP | 2012-127036 A | | 5/2012 |
| JP | 2012-202000 A | * | 10/2012 |
| JP | 2012-202000 A | | 10/2012 |
| WO | WO 97/42279 | | 11/1997 |
| WO | WO 00/06678 | | 2/2000 |
| WO | WO 01/02338 | | 1/2001 |
| WO | WO 2006/076952 | | 7/2006 |
| WO | WO2007092020 | | 8/2007 |
| WO | WO 2011/120822 A | | 10/2011 |
| WO | WO 2011/149475 | | 12/2011 |
| WO | WO 2014/092693 | | 6/2014 |

OTHER PUBLICATIONS

International Search Report and Written Opinion dated Mar. 10, 2014, for International application No. PCT/US2013/065477, filed Oct. 17, 2013 (12 pages).
International Preliminary Report on Patentability dated Sep. 24, 2015, for International application No. PCT/US2013/065477, filed Oct. 17, 2013 (8 pages).
Extended European Search Report, dated Nov. 14, 2016, for Application No. 13877679.4.
Examination report No. 1 for standard patent application, dated Feb. 10, 2017, for Australian Application No. 2013381757.
Examination report No. 1 for standard patent application, dated Aug. 10, 2017, for Japanese Application No. 2016-500101.

* cited by examiner

*Primary Examiner* — John R Hardee

(74) *Attorney, Agent, or Firm* — McAndrews, Held & Malloy, Ltd.

(57) ABSTRACT

A fabric conditioning active composition comprising an esterquat mixture of quaternized mono-, di-, and tri-esters of alkanolamine in which the tri-esterquat content of the quaternized esterquat mixture is greater than 25% by weight of the esterquat mixture, and the combined di-esterquat and tri-esterquat content in the esterquat mixture is greater than 78% by weight of the esterquat mixture. Additionally, the free fatty acid content of the composition is greater than 1% by weight based on the weight of the esterquat mixture. The fabric conditioning active composition provides high viscosity when dispersed into water at low concentrations of 0.5% to 12%, without the need for additional polymeric thickeners or other thickening additives.

16 Claims, No Drawings

FABRIC SOFTENER COMPOSITIONS

RELATED APPLICATIONS

This application is a continuation of and claims priority to U.S. application Ser. No. 14/853,500, filed on Sep. 14, 2015, now abandoned, which is a continuation of and claims priority to PCT Patent Application PCT/US2013/065477, having an International filing date of Oct. 17, 2013, which claims priority to U.S. provisional Application No. 61/789,825, filed Mar. 15, 2013. The entire specification of the provisional application referred to above is hereby incorporated by reference.

FIELD OF THE INVENTION

The present invention relates to fabric treatment compositions and methods of using and making the same.

BACKGROUND OF THE INVENTION

As the percent of fabric softener active compound goes down in a liquid fabric softening composition, the viscosity of the liquid fabric softening composition also goes down. However, thickness is a desirable property in liquid fabric softening compositions. Thickness connotes quality and richness of the product. In many countries in the world, liquid fabric softening compositions (usually aqueous dispersions of fabric softener actives) are made with low concentrations (e.g. 0.5-12%) of the fabric softener active. Often, to achieve the desired viscosity of the aqueous dispersion, expensive polymers or additives (such as stearyl alcohol) must be added. There is a long unmet need in the market for a fabric softener active that, when dispersed in water at low concentrations, affords high viscosity dispersions without the need for a significant, if any, amount of polymer or thickening additive.

In WO 2007/092020 fabric softener active compositions are described wherein the amount of tri-ester quat (TEQ), as a percentage of the combined total (to 100%) of mono-ester quat (MEQ), di-ester quat (DEQ) and triester quat, is greater than 25%. However, a disadvantage is that the inventive compositions require that the free fatty acid be less than 1% in all cases. In order to achieve a free fatty acid value of less than 1%, long reaction times are required which utilize a significant amount of energy considering reactions to produce fabric softener actives are run between 160 and 210 degrees Celsius. When longer reaction times are employed, in order to achieve a certain high level of TEQ, less biorenewable, sustainable fatty acid (or methyl ester) is needed and more non-renewable, petroleum-based amine hub, e.g. triethanolamine (TEA), is required. WO2007/092020 also teaches that the iodine value (IV) of the feed used to provide the alkyl chains should be 20 or below—in general, the lower the IV of the feed, the worse the storage stability of liquid compositions made from fabric softener actives utilizing that feed, since the more saturated the fatty acids that hydrolyze (especially at elevated temperatures of the liquid fabric softener composition), the more they will crystallize and increase viscosity.

Thus, there is a need for a fabric softener active which will produce high viscosity when dispersed into water at low concentrations. There is also a need to produce the fabric softener active in the most energy efficient way possible and with maximum aqueous dispersion viscosity building potential.

SUMMARY OF THE INVENTION

It has surprisingly been found that high-viscosity liquid fabric softener compositions can be formulated using fabric softener actives containing higher levels of TEQ and higher levels of free fatty acid than previously taught in the literature.

In a first aspect, the present technology provides a liquid fabric softening composition comprising from 0.5% to 12% by weight of a fabric softening active containing an ester-quat mixture of quaternized mono-, di- and tri-ester alkanolamines, in which the tri-esterquat content of the esterquat mixture is greater than 25% by weight of the mixture; and water; wherein, when the fabric softening active is made from a 50% by weight hard, 50% by weight soft tallow fatty acid mixture, the initial viscosity of a 4% dispersion of the composition is greater than 304 cPs; and the fabric softening active contains greater than 1% free fatty acid.

In a second aspect, the present technology is directed to a method for conditioning textiles comprising, in no particular order, the steps of:

A. providing a laundry detergent or fabric softener composition comprising water, at least one anionic surfactant, and from 0.5% to 12% by weight of a fabric softening active containing an esterquat mixture of quaternized mono-, di-, and tri-ester alkanolamines, in which the tri-esterquat content of the esterquat mixture is greater than 25% by weight of the mixture, in a ratio and concentration to effectively soften and condition fabrics under predetermined laundering conditions;

B. contacting one or more articles with the composition at one or more points during a laundering process; and C. allowing the articles to dry or mechanically tumble-drying them.

In a third aspect, the present technology is directed to a fabric softening active composition comprising: a mixture of quaternized mono-, di- and tri-ester alkanolamines wherein, the combined diester quat and triester quat is greater than 78% by weight of the total esterquat mixture; the triester quat is greater than 25% by weight of the total esterquat mixture; and, the fabric softening active contains greater than 1% by weight free fatty acid. The molar ratio of fatty acid/fat to alkanolamine used to make the esterquat mixture is greater than 1.94:1, and the reaction time required to produce the esteramine which yields a triester quat content of greater than 25% and combined diester quat and triester quat content of greater than 78% after quatting is less than 6 hours and 40 minutes when the reaction is run at 190° C. and the zero time of the reaction is set at when the reaction mixture first reaches 190° C.

BRIEF DESCRIPTION OF SEVERAL VIEWS OF THE DRAWINGS

[Not Applicable]

DETAILED DESCRIPTION OF THE INVENTION

All percentages, parts, ratios, or proportions stated in this specification are by weight unless otherwise indicated.

The fabric conditioning active material of the present invention is useful, for example, in formulating liquid fabric conditioning and antistatic compositions used, for example, in a laundering process.

Esterquat Fabric Conditioning Active Material

The fabric conditioning active material of the present invention comprises an esterquat mixture of quaternized mono-ester, di-ester, and tri-ester components wherein the tri-esterquat component is greater than 25% by weight of the total esterquat mixture, up to about 55%, alternatively up to 50%, alternatively up to 45% by weight of the total esterquat mixture. Preferably, the combined di-ester quat and tri-ester quat components is greater than 78% by weight of the total esterquat mixture, up to about 98%, alternatively up to 95%, alternatively up to 93% by weight of the total esterquat mixture. (The sum of the weights of mono-esterquat, di-esterquat, and tri-esterquat is 100% by weight of the esterquat mixture.)

By mono-, di- and tri-esterquat components, it is meant that the esterquat conditioning material comprises, respectively, a mono-esterquat (an esterquat compound comprising a single ester link with a fatty hydrocarbyl chain attached thereto), a di-esterquat (an esterquat compound comprising two ester links each of which has a fatty hydrocarbyl chain attached thereto), and a tri-esterquat (an esterquat compound comprising three ester links each of which has a fatty hydrocarbyl chain attached thereto).

In this specification, a "fatty hydrocarbyl chain," such as "R" in the amine and esterquat structures in this specification, is the alkyl or alkenyl moiety of a fatty acid, having one less carbon atom than the corresponding complete fatty acid. (The final carbon atom of the complete fatty acid is the acyl carbon of the ester linkage.) For example, stearic acid has 18 carbon atoms, arranged in the molecular formula:

$$CH_3(CH_2)_{16}COOH$$

The corresponding fatty hydrocarbyl chain is $CH_3(CH_2)_{16}-$, alternatively referred to here as a $C_{17}$ alkyl moiety. If unsaturated (for example, the fatty hydrocarbyl chain of oleic acid—a monounsaturate), it would be a $C_{17}$ alkenyl moiety.

Preferably, the average chain length of the alkyl or alkenyl moiety is at least $C_{13}$, alternatively at least $C_{15}$. In one contemplated embodiment, at least 80% of the chains have a length of $C_{15}/C_{17}$ combined.

It is contemplated in one embodiment that the alkyl or alkenyl chains can be predominantly linear.

The fatty acid hydrocarbyl chain can be contributed by various starting materials, for example free fatty acids, either separately or in combinations, such as fatty acid mixtures characteristic of the fatty acid constituents of glyceride esters in natural tallow, palm oil, palm kernel oil, lard, corn oil, soybean oil or other suitable feedstocks or mixtures thereof. Other contemplated starting materials are glyceride mono-, di-, or tri-esters of fatty acids (for example, tallow or palm kernel oil), lower alkyl esters of fatty acids (for example methyl esters), acid chlorides corresponding to fatty acids, and other compounds, as is well known in the art. Again, these fatty acid derivatives may be made from a single fatty acid or mixtures of fatty acids, such as those derived from natural fatty acid feedstocks. In one contemplated embodiment, the fatty acid feedstocks contain predominately (for example 80% or more) C16 and C18 fatty acids and/or methyl esters.

The alkanolamines useful in preparing the fabric softening active generally correspond to the following general formula:

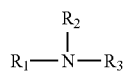

where $R_1$, $R_2$ and $R_3$ are independently selected from $C_1$-$C_6$ alkyl or hydroxy alkyl groups. Suitable alkanolamines include triethanol amine (TEA), tripropanol amine, dimethyl amino-N-(2,3-propanediol), diethylamino-N-(2,3-propanediol), methylamino-N-2-ethanol-N-2,3-propanediol, and ethylamino-N-2-ethanol-N-2,3-propanediol, and mixtures thereof. The molar ratio of fatty acid/fat to alkanolamine is greater than 1.94:1, preferably equal to or greater than 2.0:1, up to about 2.7:1, alternatively 2.5:1.

Preferred esterquats are the TEA-based esterquats.

The contemplated esterquat cationic conditioning material for use in the present technology is represented by formula (I):

(Formula I)

Each R is independently selected from a $C_{5-35}$ alkyl or alkenyl group, optionally a $C_{7-21}$ alkyl or alkenyl group, optionally a $C_{11-21}$ alkyl or alkenyl group, optionally an at least predominantly $C_{13-17}$ alkyl or alkenyl group. $R^1$ represents a $C_{1-4}$ alkyl or hydroxyalkyl group or a $C_{2-4}$ alkenyl group, T is

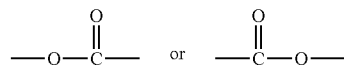

(i.e. a forward or reverse ester linkage); n is 0 or an integer selected from 1 to 4, optionally selected from 2 to 4; m is 1 for an mono-esterquat, 2 for an di-esterquat, or 3 for an tri-esterquat, and denotes the number of moieties to which it refers that pend directly from the N atom, and $X^-$ is an anionic group, such as a halide or alkyl sulphate, for example, a $C_{1-4}$ alkyl or hydroxyalkyl sulfate or a $C_{2-4}$ alkenyl sulfate. Specifically contemplated anionic groups include chloride, methyl sulphate or ethyl sulphate.

Contemplated materials within this class are esters of triethanolammonium methyl sulphate, particularly tallow or hardened tallow esters.

The tri-esterquat content of the fabric conditioning material is greater than 25% by weight. This tri-esterquat content can be provided in a variety of ways, as by using a relatively high ratio of the fatty acid to the starting alkanolamine in the reaction mixture, using an optimal amount of a suitable catalyst in the reaction mixture for promoting triester formation, raising the temperature of the reaction mixture relatively slowly, and other expedients known to the skilled person.

The contemplated di-esterquat content of the esterquat mixture is at most 70%, optionally at most 60%, optionally at most 53%, by weight of the esterquat mixture such that the combination of di-ester quat and tri-esterquat is greater than 78% by weight of the esterquat mixture.

The weight percentages of the mono-, di-, and tri-esterquats in the esterquat mixture are reported on the basis of the total weight of the three. Thus, the sum of these three percentages is 100%. The weight percentages of free amine and fatty acid in the esterquat mixture are also stated here based on the total weight of mono-, di-, and tri-esterquats in the esterquat mixture.

The compositions should contain greater than 1% by weight of free fatty acid based on the fabric conditioning material. A free fatty acid content of greater than 1% can be provided, for example, by reacting a fatty acid or a parent fatty acyl compound (such as a glyceride, alkyl ester, or acid chloride) and trialkanolamine at a reaction temperature of about 190° C. or less and at a reaction time of less than 6 hours and 40 minutes when the reaction temperature is 190° C. The free fatty acid content can be up to 10%, alternatively up to 8% based on the weight of the fabric conditioning active.

Iodine Value of the Parent Fatty Acyl Group or Acid

The iodine value of the parent fatty acyl compound or acid from which the esterquat fabric conditioning material is formed is from 1 to 100, preferably from 5 to 80, alternatively from 10 to 60, alternatively from 15 to 55, alternatively from 20 to 50. It is therefore contemplated that the alkyl or alkenyl carbon chains contain at least some unsaturation.

The iodine value represents the mean iodine value of the parent fatty acyl compounds or fatty acids of all of the esterquat materials present. In the context of the present invention, the iodine value of the parent fatty acyl compound or acid, from which the fabric conditioning material is formed, is defined as the number of grams of iodine which react with 100 grams of the parent compound. The method for calculating the iodine value of a parent fatty acyl compound/acid is known in the art and comprises dissolving a prescribed amount (from 0.1-3 g) into about 15 ml chloroform. The dissolved parent fatty acyl compound/fatty acid is then reacted with 25 ml of iodine monochloride in acetic acid solution (0.1M). To this, 20 ml of 10% potassium iodide solution and about 150 ml deionized water are added. After addition of the halogen has taken place, the excess of iodine monochloride is determined by titration with sodium thiosulfate solution (0.1M) in the presence of a blue starch indicator powder. At the same time a blank is determined with the same quantity of reagents and under the same conditions. The difference between the volume of sodium thiosulfate used in the blank and that used in the reaction with the parent fatty acyl compound or fatty acid enables the iodine value to be calculated.

Broadly speaking, the conditioning active compositions of the present invention, also known as esterquats, are made by combining a fatty acid source and an alkanolamine, typically at a starting temperature at which the fatty acid source is molten, optionally adding a catalyst, then heating the reaction mixture while drawing vacuum until the desired endpoint(s), such as acid value and final alkalinity value, are reached. A typical acid value endpoint is in the range of about 0.05 to about 0.06 meq/g. A desired alkalinity value will depend upon the ratio of fatty acid/fat to alkanolamine, but typically will be about 1.30 to about 1.90 meq/g. The resulting esteramine intermediate is then quaternized using an alkylating agent, yielding an esterquat product. The esterquat product is a mixture of quaternized monoester, diester, and triester components and optionally some amount of one or more reactants, intermediates, and byproducts, including but not limited to free amine and free fatty acid or parent fatty acyl compounds.

The fabric conditioning active compositions of the present invention can be formulated with water and other ingredients to provide fabric conditioner compositions for use in the rinse cycle of a domestic or commercial laundry process. Additional ingredients useful in formulating fabric conditioner compositions are known to those of skill in the art.

Some examples of other ingredients can be found in WO2007/092020, which is herein incorporated by reference.

Liquid Carrier

The fabric conditioner compositions can optionally further comprise a liquid carrier. The liquid carrier employed in the instant compositions is preferably water due to its low cost, relative availability, safety, and environmental compatibility. The level of water in the liquid carrier is more than about 50%, optionally more than about 80%, alternatively more than about 85%, by weight of the carrier. The level of liquid carrier is greater than about 50%, optionally greater than about 65%, alternatively greater than about 70%. Mixtures of water and a low molecular weight, for example <100, organic solvent, for example a lower alcohol such as ethanol, propanol, isopropanol or butanol are useful as the carrier liquid. Low molecular weight alcohols including monohydric, dihydric (glycol, etc.) trihydric (glycerol, etc.), and polyhydric (polyols) alcohols are also suitable carriers for use in the compositions of the present invention.

Adjunct Ingredients

Adjunct ingredients may be added to the compositions of the present technology. The term "adjunct ingredient" includes: perfumes, dispersing agents, stabilizers, pH control agents, metal ion control agents, colorants, brighteners, dyes, odor control agent, pro-perfumes, cyclodextrin, perfume, solvents, soil release polymers, preservatives, antimicrobial agents, chlorine scavengers, anti-shrinkage agents, fabric crisping agents, spotting agents, anti-oxidants, anti-corrosion agents, bodying agents, drape and form control agents, smoothness agents, static control agents, wrinkle control agents, sanitization agents, disinfecting agents, germ control agents, mold control agents, mildew control agents, antiviral agents, antimicrobials, drying agents, stain resistance agents, soil release agents, malodor control agents, fabric refreshing agents, chlorine bleach odor control agents, dye fixatives, dye transfer inhibitors, color maintenance agents, color restoration, rejuvenation agents, anti-fading agents, whiteness enhancers, anti-abrasion agents, wear resistance agents, fabric integrity agents, anti-wear agents, and rinse aids, UV protection agents, sun fade inhibitors, insect repellents, anti-allergenic agents, enzymes, flame retardants, water proofing agents, fabric comfort agents, water conditioning agents, shrinkage resistance agents, stretch resistance agents, and combinations thereof.

The liquid fabric softening compositions of the present technology achieve a high initial viscosity when the fabric softening active is present in an amount from 0.5 to 12%, preferably 1.5% to 10%, more preferably 2% to 8%, most preferably 3% to 6% by weight of esterquat material (active ingredient) based on the total weight of the composition. The initial viscosity, as used herein, is determined by taking viscosity measurements of the liquid fabric softener compositions after 24 hours on a Brookfield DV-II+ Pro Viscometer with an RVT spindle #4 at 50 rpm at 70° F. As a benchmark illustrative of a typical fabric softener within the scope of the present technology, for a liquid fabric softening composition comprising 4% by weight fabric softening active, formulated with a fabric softener active made from a 50% hard, 50% soft tallow fatty acid mixture, the initial viscosity is greater than 304 cPs, alternatively, greater than 310 cPs, alternatively greater than 325 cPs, alternatively greater than 350 cPs. In general, for liquid fabric softening compositions containing an amount of fabric softening active that is less than 4% by weight, the initial viscosity is less than 304 cPs, and for liquid fabric softening compositions containing an amount of fabric softening active that is more than 4% by weight, the initial viscosity is greater than 304 cPs. The initial viscosities can range up to about 5000 cPs, alternatively up to 4000 cPs, alternatively up to 3000 cPs, alternatively up to 2000 cPs. These high initial viscosities are achieved without the need for polymeric thickeners or other thickening additives, such as, for example, stearyl alcohol, long-chain diols, ceramides, or fatty acids. The liquid fabric softening compositions have good storage stability, even under elevated temperature conditions, and provide good fabric softening properties.

Methods of Making Fabric Softener Dispersions

Making the liquid fabric softener composition entails slowly mixing the molten quat which is at 80° C. or less into the liquid, preferably water, which has been heated to 70° C. or less with agitation. The dispersion is then mixed for several minutes more while it is allowed to cool to room temperature. The approach described here is not intended to be limiting as to how the dispersion can be made. Dispersion production can follow many approaches and is well known to those skilled in the art. As the temperature of the fabric softener active system is increased, viscosity decreases. Therefore, 80° C. will be the point of lowest viscosity yet at the maximum temperature which will still minimize chemical degradation in storage.

Methods of Using Fabric Softener Compositions

The fabric softening compositions of the present technology are suitable for use in the rinse cycle of a laundry process, in particular, the rinse cycle of a domestic or industrial automatic laundry washing machine or a hand washing laundry rinse basin. For example, the fabric softening composition can be dispensed from a fabric softener dispenser that is integral to the automatic laundry washing machine at the appropriate time during the laundry process. The fabric softening composition is added to the dispenser in an amount effective to soften and condition fabric articles under predetermined laundering conditions. At one or more points during the laundering process, the fabric softening composition is dispensed from the dispenser and contacts the fabric articles to soften and condition the fabrics. Following the laundering process, the fabric articles are allowed to dry or are mechanically tumbled dry.

Alternatively, the fabric softening composition can be used in a hand washing laundry process wherein the fabric softening composition is added to one or more rinse bath solutions for manually rinsing fabric articles in a hand washing laundry process. The fabric softening composition is added to the rinse bath solution in an amount effective to soften and condition the fabric articles. Following the laundering process, the fabric articles are allowed to dry or are mechanically tumbled dry.

The following examples will more fully illustrate the embodiments of the present technology. All parts, percentages and proportions referred to herein and in the appended claims are by weight unless otherwise illustrated. Physical test methods are described below.

EXAMPLES

Tallow Fatty Acid-Based Esterquat Synthesis: The desired amount of tallow fatty acid was placed into a 2-liter glass reactor equipped with mechanical stirring, a distillation column and nitrogen blanketing. Fabric softener actives 1, 3-8 and 10 in the examples below were made with a 50:50 weight percent mixture of fully hardened ("hard") and, "as is", non-hydrogenated ("soft") tallow fatty acid; Prophetic fabric softener actives 1 and 2 in the examples below are envisioned to be made with a 50:50 weight percent mixture of fully hardened ("hard") and as is, non-hydrogenated ("soft") tallow fatty acid; fabric softener actives 11 and 12 in the examples below were made with a 28:72 weight percent mixture of fully hardened ("hard") and, "as is", non-hydrogenated ("soft") tallow fatty acid; fabric softener actives 13 and 14 in the examples below were made with a 80:20 weight percent mixture of fully hardened ("hard") and, "as is", non-hydrogenated ("soft") tallow fatty acid. Antioxidant 1010, a tetrakis [methylene-3 (3',5'-di-tert-butyl-4-hydroxyphenyl)propionate]methane (commercially available from Mayzo, Inc. Suwanee, Ga.) and phosphorous acid were added. TEA was added at the desired amount. Nitrogen was regulated and sub-surface sparged at a rate of 150 mL/min. The mixture was heated until a temperature of 190° C. was reached. As water distilled, the reaction mixture was tested for residual fatty acid using 0.1 N KOH in methanol until the target amount of free fatty acid was achieved.

The produced ester amine mixture was then added to a flask equipped with nitrogen blanketing, mechanical stirring and a reflux condenser. At 50° C., the quatting agent, dimethyl sulfate, was added at the desired amount to the flask at a rate to control the exotherm. Methyl chloride can also be used as the quatting agent. Isopropanol was added to the flask, and the reaction was cooled to 72° C. Sodium chlorite was added to the flask at the desired amount for bleaching followed by butylated hydroxytoluene as an antioxidant and citric acid monohydrate as a pH control agent.

Palm Fatty Acid-Based Esterquat Synthesis: The desired amount of palm fatty acid was placed into a 2-liter glass reactor equipped with mechanical stirring, a distillation column and nitrogen blanketing. Fabric softener actives 2 and 9 were made with a 50:50 weight percent mixture of fully hardened ("hard") and, "as is", non-hydrogenated ("soft") palm fatty acid. Antioxidant 1010 and phosphorous acid were added. TEA was added at the desired amount. Nitrogen was regulated and sub-surface sparged at a rate of 150 mL/min. The mixture was heated until a temperature of 175° C. was reached. As water distilled, the reaction mixture was tested for residual fatty acid using 0.1 N KOH in methanol until the target amount of free fatty acid was achieved.

The produced esteramine mixture was then added to a flask equipped with nitrogen blanketing, mechanical stirring and a reflux condenser. At 50° C., the quatting agent, dimethyl sulfate, was added at the desired amount to the flask at a rate to control the exotherm. Methyl chloride can also be used as the quatting agent. Isopropanol was added to the flask, and the reaction was cooled to 72° C. Sodium chlorite was added to the flask at the desired amount for bleaching followed by butylated hydroxytoluene as an antioxidant and citric acid monohydrate as a pH control agent.

Esterquat weight percent method: Dilute esterquat solutions were prepared by dissolving around 100 mg of esterquat in about 2 mL of a 2:1 mixture of acetone-d6 and chloroform-d for analyzing FSAs 1-10; a 1:1 mixture of acetone-d6 and chloroform-d was used to analyze FSAs 11-14. Proton NMR spectra of the solutions are collected using standard proton acquisition parameters with a 15 second relaxation delay. The esterquat peaks are identified and the spectrum is integrated. The normalized weight percents of the MEQ, DEQ and TEQ are calculated from their integrated areas.

Free fatty acid determination in the fabric softener active composition:

a. The Acid Value is determined for the esteramine using a colorimetric titration to a pink endpoint using phenolphthalein indicator
b. The Free Fatty Acid % is determined for the esteramine using the Molecular Weight for the Fatty Acid (i.e. 272 g/mol) Esteramine Free Fatty Acid %=Acid Value meq/g*(MW Fatty Acid/10)
c. The Free Fatty Acid % for the esterquat is determined using the percentage of esteramine in the esterquat formulation (i.e. 72%) Esterquat Free Fatty Acid %=Esteramine Free Fatty Acid %*Percentage of esteramine in esterquat.

This is the same method that was used to determine the free fatty acid content reported in WO2007/092020.

Making the liquid fabric softener compositions: Liquid compositions were made by heating water from 35° C. to 55° C. in a glass beaker equipped with an Ika Eurostar mixer and blade with a 2.5" diameter and then slowly adding the molten FSA while agitating between 100-600 rpm. After all the FSA was added, agitation was continued for another 20 minutes.

Initial Viscosity Determination: viscosity measurements of the liquid fabric softener compositions were taken after 24 hours on a Brookfield DV-II+ Pro Viscometer with an RVT spindle #4 at 50 rpm at 70° F. Viscosity after storage at certain temperatures was done using the same Brookfield conditions and the sample was allowed to equilibrate to room temperature before taking the reading.

Comparative Example 1

| FSA | Monoester quat | Diester quat | Triester quat |
|---|---|---|---|
| 1 (TFA-Based) | 30.4 | 56.4 | 13.3 |
| 2 (PFA-Based) | 33.1 | 54.7 | 12.1 |

4% Formulations 1 and 2, were made from fabric softener actives 1 and 2, respectively:

| Formulation | Initial Viscosity (cPs) |
|---|---|
| 1 | 48 |
| 2 | 28 |

With only 13.3% and 12.1% TEQ, respectively, fabric softener actives 1 and 2 afford only very low viscosity 4% aqueous dispersions.

Fabric softener actives 1 and 2 and Formulations 1 and 2 are examples of compositions which fall outside the scope of this invention.

Example 2

| FSA | FFA | Reaction Time | FA:TEA Ratio | MEQ | DEQ | TEQ |
|---|---|---|---|---|---|---|
| 3 (TFA-Based) | 0.74% | 7 h 45 m | 2.0:1 | 15.9 | 54.6 | 29.5 |
| 4 (TFA-Based) | 3.9% | 1 h 55 m | 2.2:1 | 14.1 | 54.1 | 31.8 |

4% Formulations 3 and 4 were made from fabric softener actives 3 and 4, respectively:

| Formulation | Viscosity (cPs) |
|---|---|
| 3 | 400 |
| 4 | 440 |

Fabric softener active 3 has a long reaction time relative to fabric softener active 4 and both afford about the same level of TEQ and combined DEQ and TEQ. Fabric softener active 4 utilizes more biorenewable ingredient (fatty acid) relative to the petroleum-based amine hub (TEA) than does fabric softener active 3. Even though both Formulations are based on fabric softener actives with similar TEQ and DEQ levels, Formulation 4 has higher viscosity than Formulation 3. Without wishing to be bound by theory, it is believed that the higher level of FFA in FSA 4 leads to better viscosity build in the aqueous dispersion (Formulation 4) than when an analogous aqueous dispersion is made from FSA 3, having a free fatty acid amount of less than 1% by weight.

Fabric softener active 3 and Formulation 3 are examples of compositions which fall outside the scope of this invention.

Fabric softener active 4 and Formulation 4 are examples of compositions which fall within the scope of this invention.

Example 3

| FSA | FFA | Reaction Time | FA:TEA Ratio | MEQ | DEQ | TEQ |
|---|---|---|---|---|---|---|
| 5 (TFA-Based) | 0.6% | 16 h 35 m | 2.3:1 | 8.3 | 47.2 | 44.5 |
| 6 (TFA-Based) | 2.5% | 4 h 15 m | 2.4:1 | 8.9 | 52.2 | 39.0 |

4% Formulations 5 and 6 were made from fabric softener actives 5 and 6, respectively:

| Formulation | Initial Viscosity (cPs) |
|---|---|
| 5 | 812 |
| 6 | 892 |
| | Viscosity after 12 weeks at 50 C. (cPs) |
| 5 | 116 |
| 6 | 508 |

Fabric softener active 5 has a long reaction time relative to fabric softener active 6 and both afford about the same level of TEQ and combined DEQ and TEQ. Fabric softener active 6 utilizes more biorenewable ingredient (fatty acid) relative to the petroleum-based amine hub (TEA) than does fabric softener active 5. Even though both Formulations are based on fabric softener actives with similar TEQ and DEQ levels, Formulation 6 has higher viscosity than Formulation 5. Without wishing to be bound by theory, it is believed that the higher level of free fatty acid in fabric softener active 6 leads to better viscosity build in the aqueous dispersion (Formulation 6) than when an analogous aqueous dispersion is made from fabric softener active 5. Formulation 6 also retains its viscosity better than Formulation 5 after extended storage at elevated temperature.

Fabric softener active 5 and Formulation 5 are examples of compositions which fall outside the scope of this invention.

Fabric softener active 6 and Formulation 6 are examples of compositions which fall within the scope of this invention.

Example 4

| FSA | FFA | MEQ | DEQ | TEQ |
|---|---|---|---|---|
| 7 (TFA-Based) | 0.6% | 19.9 | 54.6 | 25.5 |
| Prophetic 1 (TFA-Based) | >1% | 19.9 | 54.6 | 25.5 |

| Formulation (4% Aqueous Dispersion) | Viscosity (cPs) |
|---|---|
| 7 | 304 |
| Prophetic 1 (TFA-Based) | >304 |

Fabric softener active 7 and Formulation 7 are examples of compositions which fall outside the scope of this invention.

Prophetic fabric softener active 1 and Prophetic Formulation 1 are examples of compositions which fall within the scope of this invention.

Example 5

| FSA | FFA | MEQ | DEQ | TEQ |
|---|---|---|---|---|
| 8 (TFA-Based) | 1.25% | 8.5 | 48.9 | 42.6 |
| 9 (PFA-Based) | 5.59% | 9.5 | 48.6 | 41.9 |

| Formulation (4% Aqueous Dispersion) | Viscosity (cPs) |
|---|---|
| 8 | 886 |
| 9 | 848 |

Fabric softener actives 8 and 9 and Formulations 8 and 9 are examples of compositions which fall within the scope of this invention.

Example 6

| FSA | FFA | Reaction time | FA:TEA Ratio | TEQ |
|---|---|---|---|---|
| 10 (TFA-Based) | <1% | 6 h 40 m | 1.94:1 | 24.9 |
| Prophetic 2 (TFA-based) | >1% | <6 h 40 m | >1.94:1 | >25.0 |

Fabric softener active 10 is an example of a composition which falls outside the scope of this invention.

Prophetic fabric softener active 2 is an example of a composition which falls within the scope of this invention.

Example 7

| FSA | FFA | MEQ | DEQ | TEQ |
|---|---|---|---|---|
| 11 (TFA-Based) | 2.0% | 14.9 | 55.6 | 29.5 |
| 12 (TFA-Based) | 0.83% | 17.4 | 53.5 | 29.1 |

4% Formulations 10 and 11 were made from fabric softener actives 11 and 12, respectively:

| Formulation (4% Aqueous Dispersion) | Initial Viscosity (cPs) |
|---|---|
| 10 | 180 |
| 11 | 104 |

5% Formulations 12 and 13 were made from fabric softener actives 11 and 12, respectively:

| Formulation (5% Aqueous Dispersion) | Initial Viscosity (cPs) |
|---|---|
| 12 | 244 |
| 13 | 152 |

FSA 11 and Formulations 10 and 12 are examples of compositions which fall within the scope of this invention.

Example 8

| FSA | MEQ | DEQ | TEQ |
|---|---|---|---|
| 13 (TFA-Based) | 18.6 | 53.6 | 27.8 |
| 14 (TFA-Based) | 21.0 | 55.7 | 23.3 |

3% Formulations 14 and 15 were made from FSAs 13 and 14, respectively

| Formulation (3% Aqueous Dispersion) | Initial Viscosity (cPs) |
|---|---|
| 14 | 532 |
| 15 | 256 |

FSA 13 and Formulation 14 are examples of compositions which fall within the scope of this invention.

The present technology is now described in such full, clear and concise terms as to enable a person skilled in the art to which it pertains, to practice the same. It is to be understood that the foregoing describes preferred embodiments of the present technology and that modifications may be made therein without departing from the spirit or scope of the present technology as set forth in the appended claims. Further the examples are provided to not be exhaustive but illustrative of several embodiments that fall within the scope of the claims.

What is claimed is:
1. A method of making an esterquat fabric softening active comprising the steps of:
   a. reacting triethanolamine (TEA) with a fatty acid or methyl ester thereof in a molar ratio of fatty acid or methyl ester to TEA of greater than 1.94:1, at a reaction temperature of about 190° C. or less and a reaction time of less than 6 hours and 40 minutes, to obtain an esteramine intermediate;
   b. adding an alkylating agent to the esteramine intermediate to obtain an esterquat fabric softening active comprising a quaternized mixture of mono-, di-, and tri-ester ethanolamines, in which the tri-esterquat content of the esterquat mixture is greater than 25% by weight of the mixture, the combined di-esterquat and tri-esterquat content is greater than 78% up to 98% by weight of the esterquat mixture, and the fabric softening active comprises at least 1.25% by weight free fatty acid.

2. The method of claim 1, wherein the molar ratio of fatty acid or methyl ester to TEA is 2.0:1 to 2.7:1.

3. The method of claim 1, wherein the fabric softening active comprises up to 10% by weight free fatty acid.

4. The method of claim 1, wherein the fatty acid or methyl ester thereof has an Iodine Value of from 20 to 80.

5. The method of claim 1, wherein the fatty acid or methyl ester thereof comprises a mixture of fully hardened and non-hydrogenated fatty acids.

6. The method of claim 5, wherein the mixture is a 50:50 weight percent mixture of fully hardened and non-hydrogenated fatty acids.

7. The method of claim 5, wherein the mixture is an 80:20 weight percent mixture of fully hardened and non-hydrogenated fatty acids.

8. A method of making a fabric softener composition, comprising the steps of:
   a. making a molten esterquat fabric softening active according to claim 1;
   b. mixing from 0.5% to 12% by weight, based on the weight of the fabric softener composition, of the esterquat into water which has been heated to a temperature of 35° C. to 55° C., and agitating the esterquat and water to form a dispersion;
   c. allowing the dispersion to cool to obtain the fabric softener composition.

9. The method of claim 8, wherein the molar ratio of fatty acid or methyl ester to TEA is 2:1 to 27:1.

10. The method of claim 8, wherein the fabric softening active comprises up to 10% by weight free fatty acid.

11. The method of claim 8, wherein the fatty acid or methyl ester thereof has an Iodine Value of from 20 to 80.

12. The method of claim 8, wherein the fatty acid or methyl ester thereof comprises a mixture of fully hardened and non-hydrogenated fatty acids.

13. The method of claim 12, wherein the mixture is a 50:50 weight percent mixture of fully hardened and non-hydrogenated fatty acids.

14. The method of claim 13, wherein the fabric softener composition has an initial viscosity of greater than 304 cPs at 70° F. (21° C.) when made with 4% by weight of the fabric softening active.

15. The method of claim 12, wherein the mixture is an 80:20 weight percent mixture of fully hardened and non-hydrogenated fatty acids.

16. The method of claim 8, wherein the amount of esterquat is from 1.5% to 6% by weight.

* * * * *